United States Patent
O'Lenick, Jr.

[11] Patent Number: 5,411,729
[45] Date of Patent: May 2, 1995

[54] SILICONE POLYESTER POLYMERS AS DURABLE HUMECTANTS

[75] Inventor: Anthony J. O'Lenick, Jr., Lilburn, Ga.

[73] Assignee: Siltech Inc., Norcross, Ga.

[21] Appl. No.: 195,177

[22] Filed: Feb. 14, 1994

[51] Int. Cl.$^6$ .............. A61K 7/075; A61K 7/08; C08G 77/16
[52] U.S. Cl. ................ 424/70.12; 528/26; 528/29
[58] Field of Search ........... 424/71, 70.12; 528/26, 528/29

[56] References Cited

U.S. PATENT DOCUMENTS

| | | | |
|---|---|---|---|
| 2,576,486 | 11/1951 | Speier, Jr. | 528/26 |
| 2,584,342 | 2/1952 | Goodwin, Jr. et al. | 528/26 |
| 2,842,517 | 7/1958 | Shorr | 528/26 |
| 3,449,465 | 6/1969 | Golitz et al. | 528/26 |
| 4,725,658 | 2/1988 | Thayer et al. | 528/15 |
| 5,051,489 | 9/1991 | Olenick, Jr. et al. | 528/26 |
| 5,210,133 | 5/1993 | O'Lenick, Jr. et al. | 528/26 |
| 5,235,017 | 8/1993 | O'Lenick, Jr. et al. | 528/26 |

Primary Examiner—Thurman K. Page
Assistant Examiner—Peter F. Kulkosky

[57] ABSTRACT

The invention discloses novel series of silicone polyesters which are useful as humectants for softening, conditioning and lubricating hair and skin. Compounds of the invention by are prepared by the esterification of (a) a hydroxyl containing silicone compound selected from silanol and dimethicone copolyol (b) a diacid and (c) a poly-hydroxy compound selected from the group consisting of glycerine, methyl glucoside, sorbitol and their alkoxylates and (d) optionally a fatty acid. The polyesters of the present invention allow for the formulation of personal care products in which the humectant is substantive to the hair and skin by virtue of the structure of the polyester and can be formulated into a variety of products for delivery to hair and skin.

20 Claims, No Drawings

SILICONE POLYESTER POLYMERS AS DURABLE HUMECTANTS

BACKGROUND OF THE INVENTION

1. Field of the Invention

The invention discloses novel series of silicone polyesters which are as additives to personal care products, giving unique skin and hair conditioning properties. Compounds of the invention by are prepared by the esterification of (a) a hydroxyl containing silicone compound selected from silanol and dimethicone copolyol (b) a diacid and (c) a polyhydroxyl compound selected from the group consisting of glycerine, methyl glucoside, sorbitol and their alkoxylates and (d) optionally a fatty acid.

The polyesters of the present invention allow for the formulation of personal care products in which outstanding humectant properties, conditioning and gloss can be formulated into a variety of products ranging from water soluble shampoos, to oil based skin care products. The incorporation of the poly-hydroxy compounds into the compound results in the desired humectant properties, the desired emmoiency and the desired antistatic properties, the incorporation of the silicone portion results in extended durability of the compound to the hair making it substantive to the hair for multiple washings. In a preferred embodiment, a fatty acid is incorporated into the molecule to provide improved wet combability.

2. Arts and Practices

The personal care market is a very diverse market segment which includes a number of products designed to be used on hair, skin, lips, and nails. These products include shampoos, bubble baths, pomades, conditioners, make up, hand cream, make up remover, hair relaxer, lipstick, nail polish, and many others. Some of these products are water based like shampoo others are mineral oil based like make up remover.

In addition to performing the specific cosmetic function in each type of product, there is a general need in each product type to incorporate ingredients which will help improve the condition of the hair, skin nails and lips. The desirable functions include but are not limited to; barrier properties, re-moisturization, softening, and conditioning.

One of the most important function of human skin is the protection against adverse environmental factors. Environmental factors like exposure of the skin to sun, cold or heat adversely effects the skin and minimizes the barrier property of the skin. Additionally, the application of many cosmetic products or use of soap on the skin removes the fatty layer of the skin. It is therefore highly desirable to replace the barrier properties which are removed from the skin. Lipids and other oily materials added to the skin improve the natural barrier properties of the skin and hair the skin retain moisture and feel soft. The addition of a methyl glucoside silicone polyester to the hair and skin results in moisturizing and barrier properties, which are highly desirable for personal care products.

We have discovered that the incorporation of a compound selected from the group consisting of glycerine, methyl glucoside, sorbitol and their alkoxylates into a silicone polyester in relatively low concentrations results in polyesters which can be made soluble in many different solvents and which give the beneficial properties of the glycerine, methyl glucoside, sorbitol and their alkoxylates and is durable to the hair and skin. In addition outstanding gloss can be provided. In short, low concentrations of these polyesters by virtue of their substantivity to hair and skin will provide outstanding re-moisturization properties in many varied personal care formulations.

U.S. Pat. No. 5,051,489 issued September 1991 to O'Lenick teaches that silicone waxes can be prepared via esterification of silanol compounds. These materials contain no actives.

U.S. Pat. No. 5,100,956 issued March 1992 to O'Lenick teaches that silicone compounds can be linked to proteins or amino acids through a phosphate group. This invention shows the desirability of incorporating the active protein into a molecule containing silicone, which is one of the objectives of the current invention. The O'Lenick ('956) technology is not applicable to actives which do not have nitrogen in the molecule.

THE INVENTION

Object of the Invention

It is the object of the present invention to provide a series of novel silicone polyesters which contain within the molecule an humectant functionality in a polyester. The selection of the proper silicone portion results in the ability to prepare products which have solubility in a wide range of solvents.

It is another objective of the current invention to provide a method of treating hair and skin with these polyesters. The process for treating the hair and skin comprises the contacting of the hair or skin with an effective conditioning amount of the silicone polyester. The silicone portion of the molecule is substantive to the substrate, hair and skin and binds there. The beneficial effect of the methyl glucoside is enhanced since the silicone delivers the active to the surface of the hair or skin. This prolonged intimate contact allows for enhanced performance by the active.

Summary of the Invention The present invention relates to a series of novel silicone polyester compounds. The compounds by virtue of the glycerine, methyl glucoside, sorbitol and their alkoxylates present in the molecule form effective skin and hair modifiers, providing refatting, moisturization, conditioning and softening. The compounds of the present invention are substantive to hair, skin and textile fibers.

The polyester compounds of the invention by are prepared by the esterification of (a) a hydroxyl containing silicone compound selected from silanol and dimethicone copolyol (b) a diacid and (c) a poly-hydroxyl compound selected from the group consisting of glycerine, methyl glucoside, sorbitol and their alkoxylates and (d) optionality a fatty acid.

Polyester compounds are created by the esterification reaction with the hydroxyl groups in the poly-hydroxy compound, resulting in a polymer.

It will be clearly understood that (a) the silicone compounds contain a plurality of hydroxyl groups, (b) the diacid contains two organic acid groups and (c) the poly hydroxy compound selected from the group consisting of glycerine, methyl glucoside, sorbitol and their alkoxylates contain a plurality of hydroxyl groups so that the resulting polymer is very highly branched and very high in molecular weight. These properties prevent the molecule from penetrating the skin or hair, resulting in surface modification without and irritation to the skin or eyes.

As stated the polyester compounds of the invention by are prepared by the esterification of (a) a hydroxyl containing silicone compound selected from
1. Dimethicone copolyols conforming to the following structure;

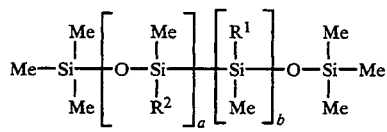

wherein;
Me is methyl;
a is an integer ranging from 2 to 20;
b is an integer ranging from 0 to 200;
$R^1$ is selected from the group consisting of methyl and phenyl;
$R^2$ is $(CH_2)_3$—O—$(CH_2$—$CH_2$—O$)_x$—$(CH_2(CH_3)CH_2$—O$)_y$—$(CH_2$—$CH_2$—O$)_z$—H
x, y, and z are independently integers ranging from 0 to 20;

2. Terminal Dimethicone copolyols conforming to the following structure;

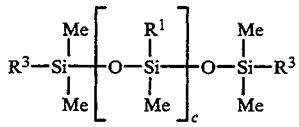

wherein;
Me is methyl;
c is an integer ranging from 1 to 200;
$R^1$ is selected from the group consisting of methyl and phenyl;
$R^3$ is —$(CH_2)_3$—O—$(CH_2$—$CH_2$—O$)_x$—$(CH_2(CH_3)CH_2$—O$)_y$—$(CH_2$—$CH_2$—O$)_z$—H and
3. Silanol compounds conforming to the following structure;

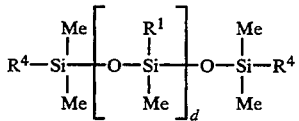

wherein;
Me is methyl;
d is an integer ranging from 10 to 1200;
$R^1$ is selected from the group consisting of methyl and phenyl;
$R^4$ is OH;
(b) a diacid selected the group consisting of;
HO—C(O)—$(CH_2)_q$—C(O)—OH,
HO—C(O)—$(CH_2)_r$—CH=CH—$(CH_2)_s$—C(O)—OH;
q is an integer from 2 to 10;
r is an integer from 2 to 10;
s in an integer from 2 to 10;
dimer acid and hydrogenated dimer acid;
(c) a poly hydroxy compound selected from the group consisting of glycerine, methyl glucoside, sorbitol and their alkoxylates.

Examples of polyhydroxy compounds useful in the practice of the invention include:

Glycerine and it's alkoxylates are items of commerce and conforms to the following structure:

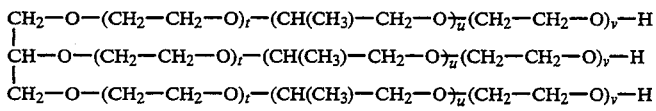

t, u and v are independently integers ranging from 0 to 20;

Methyl glucoside and it's alkoxylates are known materials marketed by a variety of manufacturers including Amerchol Corporation in Edison, N.J.. These materials conform to the following structure;

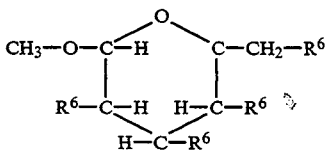

$R^6$ is —O—$(CH_2$—$CH_2$—O$)_t$—$(CH(CH_3)$—$CH_2$—O—$)_u$—$(CH_2$—$CH_2$—O$)_v$—H
t, u and v are independently integers ranging from 0 to 20;

Sorbitol and it's alkoxylates are commercially available materials and conform to the following structure;

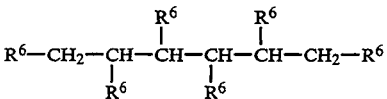

$R^6$ is —O—$(CH_2$—$CH_2$—O$)_t$—$(CH(CH_3)$—$CH_2$—O—$)_u$—$(CH_2$—$CH_2$—O$)_v$—H
t, u and v are independently integers ranging from 0 to 20;

and optionally
(d) a mono functional fatty acid conforming to the following structure;

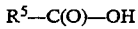
$R^5$—C(O)—OH $R^5$ is selected from the group consisting of alkyl and alkylene and has from 6 to 20 carbon atoms.

Preferred Embodiments

In a preferred embodiment said hydroxy silicone conforms to the following structure;

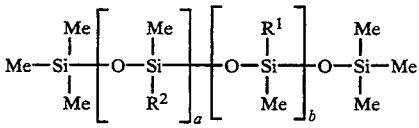

wherein;
Me is methyl;
a is an integer ranging from 2 to 20;

b is an integer ranging from 0 to 200;
R$^1$ is selected from the group consisting of methyl and phenyl;
R$^2$ is (CH$_2$)$_3$—O—(CH$_2$—CH$_2$—O)$_x$—(CH$_2$(CH$_3$)CH$_2$—O)$_y$—(CH$_2$—CH$_2$—O)$_z$—H
x, y, and z are independently integers ranging from 0 to 20.

In another preferred embodiment said hydroxy silicone conforms to the following structure;

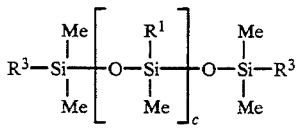

wherein;
Me is methyl;
c is an integer ranging from 1 to 200;
R$^1$ is selected from the group consisting of methyl and phenyl;
R$^3$ is —(CH$_2$)$_3$—O—(CH$_2$—CH$_2$—O)$_x$—(CH$_2$(CH$_3$)CH$_2$—O)$_y$—(CH$_2$—CH$_2$—O)$_z$—H.

In still another preferred embodiment said hydroxy silicone conforms to the following structure;

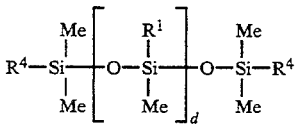

wherein;
Me is methyl;
d is an integer ranging from 10 to 1200;
R$^1$ is selected from the group consisting of methyl and phenyl;
R$^4$ is OH.

In a preferred embodiment said poly hydroxy compound conforms to the following structure:

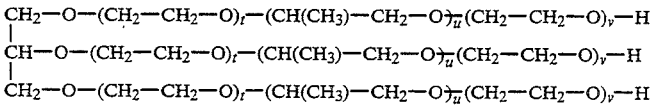

t, u and v are independently integers ranging from 0 to 20.

In another preferred embodiment said poly hydroxy compound conforms to the following structure:

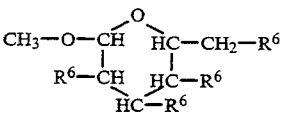

R$^6$   —O—(CH$_2$—CH$_2$—O)$_t$—(CH(CH$_3$)—CH$_2$—O—)$_u$—(CH$_2$—CH$_2$—O)$_v$—H t, u and v are independently integers ranging from 0 to 20.

In another preferred embodiment said poly hydroxy compound conforms to the following structure:

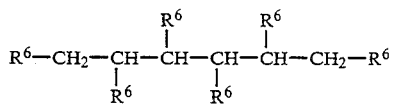

R$^6$ is —O—(CH$_2$—CH$_2$—O)$_t$—(CH(CH$_3$)—CH$_2$—O—)$_u$—(CH$_2$—CH$_2$—O)$_v$—H t, u and v are independently integers ranging from 0 to 20.

The mole ratios of Silicone:Diacid:poly hydroxy can be varied to give products of differing molecular weight. The range from 0.99:1.0:0.01 to 1.5:2.0:1.0. In a preferred embodiment the ratio ranges from 0.90:1.00:0.1 to 1.0:2.0:1.0.

In preferred embodiment mono fatty acids are reacted into the polyester. Not only does this decrease water solubility, it results in a product which forms a hydrophobic non-occlusive film.

The invention also teaches that the compounds of the present invention are useful in a process for treating hair and skin. The process contacts the hair or skin with an effective conditioning amount of the compound. In a preferred embodiment the concentration of the compound ranges from 0.05% to 25% and in a more preferred embodiment the concentration ranges from 1% to 10%. The compound can be delivered from water or a suitable solvent.

EXAMPLES

Reactants

SILICONE COMPONENT

The silicone components of the present invention are all available form Siltech Inc. Norcross Ga. They are items of commerce prepared by methods known to those skilled in the art.

Class 1 (Hydroxyl Silicone)

A. Dimethicone copolyols conforming to the following structure;

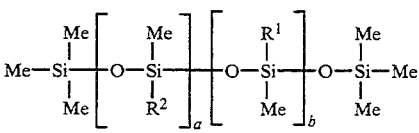

wherein;
Me is methyl;
a is an integer ranging from 2 to 20;
b is an integer ranging from 0 to 200;
R$^1$ is selected from the group consisting of methyl and phenyl;
R$^2$ is —(CH$_2$)$_3$—O—(CH$_2$—CH$_2$—O)$_x$—(CH$_2$(CH$_3$)CH$_2$—O)$_y$—(CH$_2$—CH$_2$—O)$_z$—H
x, y, and z are independently integers ranging from 0 to 20;

| Example | R$^1$ | b | a | x | y | z |
|---|---|---|---|---|---|---|
| 1 | Methyl | 29 | 4 | 0 | 0 | 8 |
| 2 | Methyl | 0 | 2 | 0 | 0 | 0 |
| 3 | Phenyl | 120 | 10 | 20 | 20 | 20 |
| 4 | Phenyl | 200 | 20 | 5 | 10 | 5 |
| 5 | Methyl | 50 | 2 | 7 | 2 | 2 |
| 6 | Methyl | 200 | 5 | 1 | 5 | 4 |

B. Terminal Dimethicone copolyols conforming to the following structure;

$$R^3-\underset{\underset{Me}{|}}{\overset{\overset{Me}{|}}{Si}}-\left[O-\underset{\underset{Me}{|}}{\overset{\overset{R^1}{|}}{Si}}\right]_c-O-\underset{\underset{Me}{|}}{\overset{\overset{Me}{|}}{Si}}-R^3$$

wherein;
Me is methyl;
c is an integer ranging from 1 to 200;
R$^3$ is selected from the group consisting of methyl and phenyl;
R$^3$ is $-(CH_2)_3-O-(CH_2-CH_2-O)_x-(CH_2(CH_3)CH_2-O)_y-(CH_2-CH_2-O)_z-H$

| Example | R$^1$ | c | x | y | z |
|---|---|---|---|---|---|
| 7 | Methyl | 1 | 0 | 0 | 10 |
| 8 | Methyl | 20 | 0 | 0 | 0 |
| 9 | Phenyl | 50 | 20 | 20 | 20 |
| 10 | Methyl | 100 | 5 | 5 | 5 |
| 11 | Methyl | 125 | 1 | 5 | 7 |
| 12 | Methyl | 200 | 0 | 0 | 20 | and
C. Silanol compounds conforming to the following structure;

$$R^4-\underset{\underset{Me}{|}}{\overset{\overset{Me}{|}}{Si}}-\left[O-\underset{\underset{Me}{|}}{\overset{\overset{R^1}{|}}{Si}}\right]_d-O-\underset{\underset{Me}{|}}{\overset{\overset{Me}{|}}{Si}}-R^4$$

wherein;
Me is methyl;
d is an integer ranging from 10 to 1200;
R$^1$ is selected from the group consisting of methyl and phenyl;
R$^4$ is OH;
Silanol Silanol compounds are well known and are marketed in the trade under many names. The compounds conforms to the following generic structure;

$$HO-\underset{\underset{Me}{|}}{\overset{\overset{Me}{|}}{Si}}-\left[O-\underset{\underset{Me}{|}}{\overset{\overset{Me}{|}}{Si}}\right]_d-O-\underset{\underset{Me}{|}}{\overset{\overset{Me}{|}}{Si}}-OH$$

Compounds of the following structure are available from Siltech Inc. Norcross, Ga. and are marketed under the Silteh S series trade names shown;

| Example | Name | "d" Value | Approximate Molecular Weight |
|---|---|---|---|
| 13 | Siltech S 701 | 10 | 1,000 |
| 14 | Siltech S 706 | 78 | 6,000 |
| 15 | Siltech S 710 | 133 | 10,000 |
| 16 | Siltech S 750 | 673 | 50,000 |
| 17 | Siltech S 790 | 1160 | 86,000 |

DIACID COMPONENT

Class 2 (Diacids)

| Example Weight | Diacid | Formula | Molecular |
|---|---|---|---|
| 18 | Adipic Acid | HO(O)C(CH2)4C(O)OH | 146 |
| 19 | Succinic Acid | HO(O)C(CH2)2C(O)OH | 118 |
| 20 | Dodecanedioic Acid | HO(O)C(CH2)10C(O)OH | 230 |

Dimer acid is produced by the high temperature cyclization of unsaturated fatty acids, most commonly tall oil fatty acid. Many U.S. Patents have been issued on the production of dimer acids. These include U.S. Pat. Nos. 2,793,219; 2,793,220; 3,100,484; 3,424,1224; and 3,632,822. These patents are incorporated herein by reference.

EXAMPLE 21

The structure of dimer acid includes each of the following;

$$CH_3-(CH_2)_8-\underset{|}{CH}-(CH2)_7-C(O)-OH$$
$$CH_3-(CH2)_7-CH=C-(CH2)_7-C(O)-OH$$

monocyclic bicyclic

The commonality to the above product is the presence of two organic acid groups. Typically, the composition is

| Type | % by weight |
|---|---|
| Acyclic | 15 |
| Monocyclic | 70 |

| Type | % by weight |
| --- | --- |
| Bicyclic | 15 |

EXAMPLE 22

Dimer acid is hydrogenated to remove the double bond to give;

$$CH_3-(CH_2)_8-CH-(CH_2)_7-C(O)-OH$$
$$CH_3-(CH_2)_7-CH=C-(CH_2)_7-C(O)-OH$$

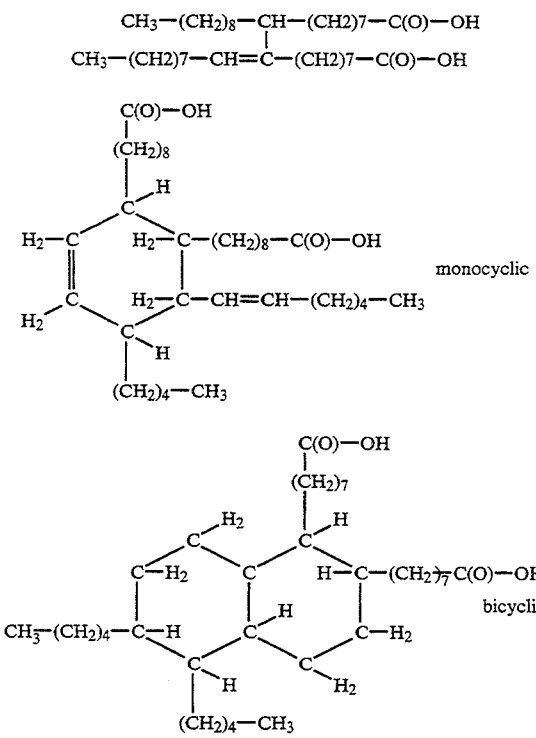

monocyclic bicyclic

Class 3 POLY-HYDROXYL COMPONENT
Glycerine and it's alkoxylates

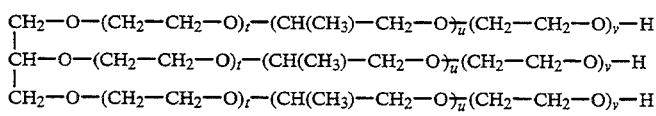

t, u and v are independently integers ranging from 0 to 20;

| Example | t | u | v |
| --- | --- | --- | --- |
| 23 | 0 | 0 | 0 |
| 24 | 10 | 10 | 10 |
| 25 | 20 | 20 | 20 |
| 26 | 0 | 20 | 0 |

Methyl glucoside and it's alkoxylates conforms to the following structure;

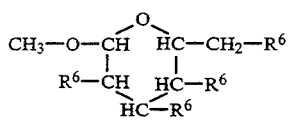

$R^6$ is $-O-(CH_2-CH_2-O)_t-(CH(CH_3)-CH_2-O-)_u-(CH_2-CH_2-O)_v-H$ t, u and v are independently integers ranging from 0 to 20;

| Example | t | u | v |
| --- | --- | --- | --- |
| 27 | 0 | 0 | 0 |
| 28 | 20 | 20 | 20 |
| 29 | 0 | 20 | 0 |

Sorbitol and it's alkoxylates conforms to the following structure:

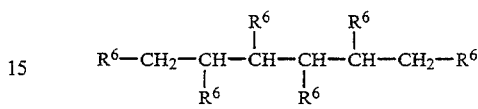

$R^6$ is $-O-(CH_2-CH_2-O)_t-(CH(CH_3)-CH_2-O-)_u-(CH_2-CH_2-O)_v-H$ t, u and v are independently integers ranging from 0 to 20;

| Example | t | u | v |
| --- | --- | --- | --- |
| 30 | 0 | 0 | 0 |
| 31 | 10 | 10 | 10 |
| 32 | 20 | 20 | 20 |
| 33 | 0 | 20 | 0 |

Class 4 FATTY ACID COMPONENT

| Example | Fatty Acids | Formula | Molecular Weight |
| --- | --- | --- | --- |
| 34 | Lauric | C12 (Saturated) | 200 |
| 35 | Myristic | C14 (Saturated) | 228 |
| 36 | Stearic | C18 (Saturated) | 284 |
| 37 | Oleic | C18 (single unsaturation) | 282 |
| 38 | Linoleic | C18 (double unsaturation) | 280 |

General Reaction Conditions

The esterification can be run without catalyst; however, when no catalysts used reaction rates are less efficient. Standard esterification catalysts are generally used at concentrations of between 0.05% to 0.50% with a preferred range of 0.1% to 0.3%. Catalysts which are effective include but are not limited to; sulfuric acid, p-toluene sulfonic acid, methane sulfonic acid, tin metal, zinc metal, titanium metal, organo titianates, organo tin compounds, organo zinc compounds, zinc oxide, magnesium oxide, calcium oxide, etc.. The most preferred catalyst is stannous oxylate. The reaction is conducted at between 140° and 240° C. under an inert nitrogen blanket. The nitrogen blanket preserves the color. Preferred temperature range is between 180° and 210° C. Water is removed from the reaction which is done using a nitrogen sparge or vacuum.

General Procedure

Into a suitable round bottom, three neck flask equipped with a Dean Stark trap, a thermometer and a nitrogen sparge is added the specified amount of the specified silicone compound (examples 1-17), 0.25% by weight of the total batch charged of stannous oxylate and the specified amount of the specified diacid (example 18-22) and the specified amount of the specified hydroxy material (examples 23-33). Finally the specified amount of the specified acid (example 34-38) is added (if any). The reaction mass is blanketed with nitrogen, and heated to 180° and 200° C. Once the reaction temperature reaches 130° C. water begins to boil off and is collected in the Dean Stark Trap. Within four to five hours the theoretical water is collected off and the acid value is very low. The product is used without additional purification.

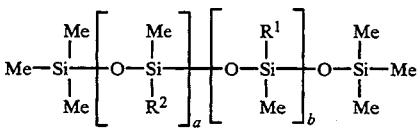

wherein;
Me is methyl;
a is an integer ranging from 2 to 20;
b is an integer ranging from 0 to 200;

|  | Silicone Component | | Diacid Component | | Polyhydroxy Component | | Fatty Acid Component | |
|---|---|---|---|---|---|---|---|---|
| Example | Ex. #/ | Gms | Ex. #/ | Gms | Ex. #/ | Gms | Ex. #/ | Gms |
| 38 | 1 | 999.9 | 18 | 146.0 | 23 | 89.0 | None | |
| 39 | 2 | 140.0 | 18 | 146.0 | 23 | 89.0 | None | |
| 40 | 3 | 4685.0 | 19 | 118.0 | 24 | 1556.0 | None | |
| 41 | 4 | 2890.0 | 20 | 230.0 | 25 | 3026.0 | None | |
| 42 | 5 | 2506.0 | 21 | 600.0 | 26 | 1266.0 | None | |
| 43 | 6 | 3586.0 | 22 | 600.0 | 27 | 60.0 | None | |
| 44 | 7 | 535.0 | 18 | 146.0 | 28 | 2999.9 | None | |
| 45 | 8 | 798.0 | 19 | 118.0 | 29 | 1240.0 | None | |
| 46 | 9 | 4848.0 | 20 | 230.0 | 30 | 33.0 | None | |
| 47 | 10 | 4493.0 | 21 | 600.0 | 31 | 1503.0 | None | |
| 48 | 11 | 5530.0 | 22 | 600.0 | 32 | 2973.0 | None | |
| 49 | 12 | 8338.0 | 18 | 146.0 | 33 | 1213.0 | None | |
| 50 | 13 | 500.0 | 19 | 118.0 | 23 | 45.0 | None | |
| 51 | 14 | 3000.0 | 20 | 230.0 | 24 | 789.0 | None | |
| 52 | 15 | 5000.0 | 21 | 600.0 | 25 | 1513.0 | None | |
| 53 | 16 | 25000.0 | 22 | 600.0 | 26 | 633.0 | None | |
| 54 | 17 | 43000.0 | 18 | 146.0 | 27 | 30.0 | None | |
| 55 | 1 | 999.0 | 19 | 118.0 | 28 | 3000.0 | 34 | 20.0 |
| 56 | 2 | 140.0 | 20 | 230.0 | 29 | 1240.0 | 35 | 23.0 |
| 57 | 3 | 4684.0 | 21 | 600.0 | 30 | 33.0 | 36 | 29.0 |
| 58 | 4 | 2488.0 | 22 | 600.0 | 31 | 1503.0 | 37 | 29.0 |
| 59 | 5 | 2506.0 | 18 | 146.0 | 32 | 2973.0 | 38 | 28.0 |
| 60 | 6 | 3568.0 | 19 | 118.0 | 33 | 1213.0 | 34 | 20.0 |
| 61 | 7 | 535.0 | 20 | 230.0 | 23 | 89.0 | 35 | 23.0 |
| 62 | 8 | 798.0 | 21 | 600.0 | 24 | 1556.0 | 36 | 29.0 |
| 63 | 9 | 4838.0 | 22 | 600.0 | 25 | 3026.0 | 37 | 29.0 |
| 64 | 10 | 4493.0 | 18 | 146.0 | 26 | 1266.0 | 38 | 28.0 |
| 65 | 11 | 5330.0 | 19 | 118.0 | 27 | 60.0 | 34 | 40.0 |
| 66 | 12 | 8338.0 | 20 | 230.0 | 28 | 3000.0 | 35 | 46.0 |
| 67 | 13 | 500.0 | 21 | 600.0 | 29 | 1240.0 | 36 | 60.0 |
| 68 | 14 | 3000.0 | 22 | 600.0 | 30 | 33.0 | 37 | 60.0 |
| 69 | 15 | 5000.0 | 18 | 146.0 | 31 | 1503.0 | 38 | 59.0 |
| 70 | 16 | 25000.0 | 19 | 118.0 | 32 | 2973.0 | 34 | 20.0 |
| 71 | 17 | 43,000.0 | 20 | 230.0 | 33 | 1213.0 | 35 | 22.8 |

Gms is being used as a abbreviation for grams.

APPLICATIONS EXAMPLES

The compounds of the present invention are durable to the hair and act as humectants over a period of five washes. They keep the hair moist and easily styled as well as conditioned.

The polyesters of the present invention allow for the formulation of personal care products in which the humectant is substantive to the hair and skin by virtue of the structure of the polyester and can be formulated into a variety of products for delivery to hair and skin.

What is claimed:
1. A silicone polyester prepared by the esterification reaction of:
(a) a hydroxyl containing silicone compound selected from dimethicone copolyol conforming to the following structure;

$$\text{Me}-\underset{\underset{\text{Me}}{|}}{\overset{\overset{\text{Me}}{|}}{\text{Si}}}-\left[\text{O}-\underset{\underset{\text{R}^1}{|}}{\overset{\overset{\text{Me}}{|}}{\text{Si}}}\right]_c-\text{O}-\underset{\underset{\text{Me}}{|}}{\overset{\overset{\text{Me}}{|}}{\text{Si}}}-\text{R}^3$$

wherein;
Me is methyl;
c is an integer ranging from 1 to 200;
$R^1$ is selected from the group consisting of methyl and phenyl;

$R^1$ is selected from the group consisting of methyl and phenyl;
$R^2$ is $(CH_2)_3$—O—$(CH_2$—$CH_2$—O$)_x$—$(CH_2(CH_3)CH_2$—O$)_y$—$(CH_2$—$CH_2$—O$)_z$—H
x, y, and z are independently integers ranging from 0 to 20;
terminal dimethicone copolyols conforming to the following structure;

$R^3$ is $-(CH_2)_3-O-(CH_2-CH_2-O)_x-(CH_2(CH_3)CH_2-O)_y-(CH_2-CH_2-O)_z-H$ and silanol compounds conforming to the following structure;

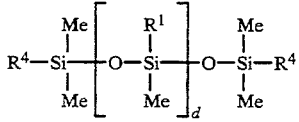

wherein;
Me is methyl;
d is an integer ranging from 10 to 1200;
$R^1$ is selected from the group consisting of methyl and phenyl;
$R^4$ is OH;
(b) a diacid selected the group consisting of;
$HO-C(O)-(CH_2)_q-C(O)-OH$,
$HO-C(O)-(CH_2)_r-CH=CH-(CH_2)_s-C(O)-OH$;
q is an integer from 2 to 10;
r is an integer from 2 to 10;
s in an integer from 2 to 10;
dimer acid and hydrogenated dimer acid;
(c) a poly-hydroxyl compound selected from the group consisting of glycerine and it's alkoxylates which conforms to the following structure:

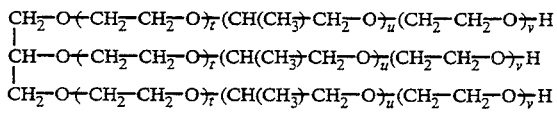

t, u and v are independently integers ranging from 0 to 20;

methyl glucoside and it's alkoxylates which conforms to the following structure:

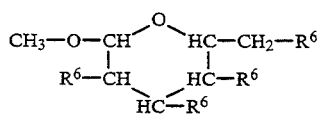

$R^6$ is $-O-(CH_2CH_2-O)_t-(CH(CH_3)-CH_2-O-)_u-(CH_2-CH_2-O)_v-H$ t, u and v are independently integers ranging from 0 to 20;

and sorbitol and it's alkoxylates which conforms to the following structure:

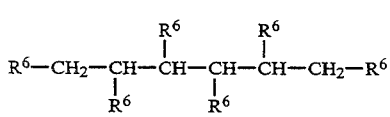

$R^6$ is $-O-(CH_2-CH_2-O)_t-(CH(CH_3)-CH_2-O-)_u-(CH_2-CH_2-O)_v-H$ t, u and v are independently integers ranging from 0 to 20;

and optional (d) a mono functional fatty acid conforming to the following structure;

$R^5-C(O)-OH$ $R^5$ is selected from the group consisting of alkyl and alkylene and has from 6 to 20 carbon atoms, said esterification reaction being conducted at a temperature of between 140° and 240° C. for a time sufficient to boil off water and form a reaction product of low acid value.

2. A compound of claim 1 wherein said hydroxy silicone conforms to the following structure;

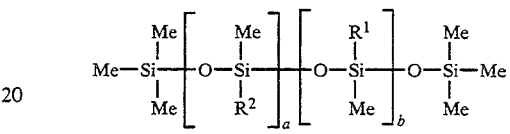

wherein;
Me is methyl;
a is an integer ranging from 2 to 20;
b is an integer ranging from 0 to 200;
$R^1$ is selected from the group consisting of methyl and phenyl;
$R^2$ is $(CH_2)_3-O-(CH_2-CH_2-O)_x-(CH_2(CH_3)CH_2-O)_y-(CH_2-CH_2-O)_z-H$
x, y, and z are independently integers ranging from 0 to 20.

3. A compound of claim 1 wherein said hydroxy silicone conforms to the following structure;

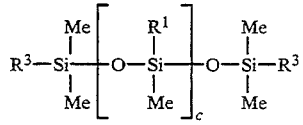

wherein;
Me is methyl;
c is an integer ranging from 1 to 200;
$R^1$ is selected from the group consisting of methyl and phenyl;
$R^3$ is $-(CH_2)_3-O-(CH_2-CH_2-O)_x-(CH_2(CH_3)CH_2-O)_y-(CH_2-CH_2-O)_z-H$.

4. A compound of claim 1 wherein said hydroxy silicone conforms to the following structure;

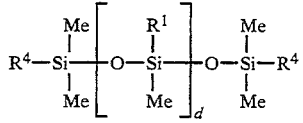

wherein;
Me is methyl;
d is an integer ranging from 10 to 1200;
$R^1$ is selected from the group consisting of methyl and phenyl;
$R^4$ is OH.

5. A compound of claim 1 wherein said polyhydroxyl compound conforms to the following structure:

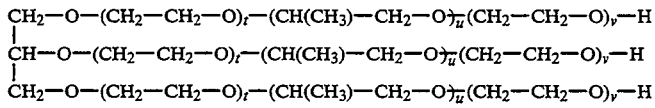

t, u and v are independently integers ranging from 0 to 20.

6. A compound of claim 1 wherein said polyhydroxyl compound conforms to the following structure:

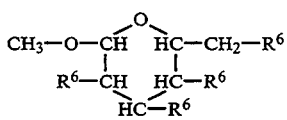

$R^1$ is —O—(CH$_2$—CH$_2$—O)$_t$—(CH(CH$_3$)—CH$_2$—O—)$_u$—(CH$_2$—CH$_2$—O)$_v$—H t, u and v are independently integers ranging from 0 to 20.

7. A compound of claim 1 wherein said polyhydroxyl compound conforms to the following structure:

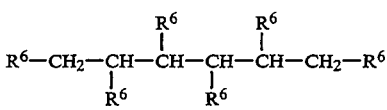

$R^6$ is —O—(CH$_2$—CH$_2$—O)$_t$—(CH(CH$_3$)—CH$_2$—O—)$_u$—(CH$_2$—CH$_2$—O)$_v$—H t, u and v are independently integers ranging from 0 to 20.

8. A compound of claim 1 wherein 2 wherein x+y+z is zero.

9. A compound of claim 1 wherein 3 wherein x+y+z is zero.

10. A compound of claim 1 wherein 4 wherein x+y+z is zero.

11. A process for treating hair which comprises contacting the hair with an effective conditioning amount of a silicone polyester prepared by the esterification reaction of (a) a hydroxyl containing silicone compound selected from dimethicone copolyol conforming to the following structure;

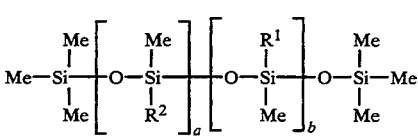

wherein;
Me is methyl;
a is an integer ranging from 2 to 20;
b is an integer ranging from 0 to 200;

$R^1$ is selected from the group consisting of methyl and phenyl;
$R^2$ is (CH$_2$)$_3$—O—(CH$_2$—CH$_2$—O)$_x$—(CH$_2$(CH$_3$)CH$_2$—O)$_y$—(CH$_2$—CH$_2$—O)$_z$—H
x, y, and z are independently integers ranging from 0 to 20;

terminal dimethicone copolyols conforming to the following structure;

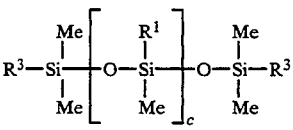

wherein;
Me is methyl;
c is an integer ranging from 1 to 200;
$R^1$ is selected from the group consisting of methyl and phenyl;
$R^3$ is —(CH$_2$)$_3$—O—(CH$_2$—CH$_2$—O)$_x$—(CH$_2$(CH$_3$)CH$_2$—O)$_y$—(CH$_2$—CH$_2$—O)$_z$—H and silanol compounds conforming to the following structure;

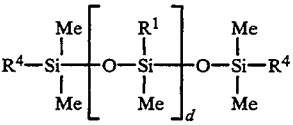

wherein;
Me is methyl;
d is an integer ranging from 10 to 1200;
$R^1$ is selected from the group consisting of methyl and phenyl;
$R^4$ is OH;

(b) a diacid selected the group consisting of;
HO—C(O)—(CH$_2$)$_q$—C(O)—OH,
HO—C(O)—(CH$_2$)$_r$—CH=CH—(CH$_2$)$_s$—C(O)—OH;
q is an integer from 2 to 10;
r is an integer from 2 to 10;
s in an integer from 2 to 10;
dimer acid and hydrogenated dimer acid;

(c) a poly-hydroxyl compound selected from the group consisting of
glycerine and it's alkoxylates which conforms to the following structure:

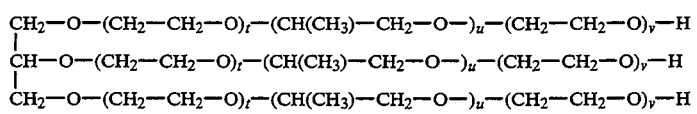

t, u and v are independently integers ranging from 0 to 20;
methyl glucoside and it's alkoxylates which conforms to the following structure:

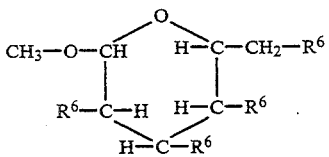

R⁶ is —O—(CH₂—CH₂—O)$_t$—(CH(CH₃)—CH₂—O—)$_u$—(CH₂—CH₂—O)$_v$—H t, u and v are independently integers ranging from 0 to 20;

and sorbitol and it's alkoxylates which conforms to the following structure:

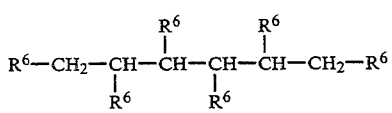

R⁶ is —O—(CH₂—CH₂—O)$_t$—(CH(CH₃)—CH₂—O—)$_u$—(CH₂—CH₂—O)$_v$—H t, u and v are independently integers ranging from 0 to 20;

and optionally (d) a mono functional fatty acid conforming to the following structure;

R⁵—C(O)—OH

R⁵ is selected from the group consisting of alkyl and

alkylene and has from 6 to 20 carbon atoms, said esterification reaction being conducted a temperature of between 140° and 240° C.

12. A process of claim 11 wherein said hydroxy silicone conforms to the following structure;

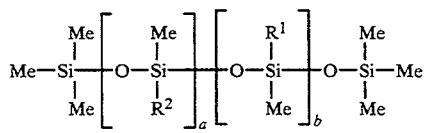

wherein;
Me is methyl;
a is an integer ranging from 2 to 20;
b is an integer ranging from 0 to 200;
R¹ is selected from the group consisting of methyl and phenyl;
R² is (CH₂)₃—O—(CH₂—CH₂—O)$_x$—(CH₂(CH₃)CH₂—O)$_y$—(CH₂—CH₂—O)$_z$—H
x, y, and z are independently integers ranging from 0 to 20.

13. A process of claim 11 wherein said hydroxy silicone conforms to the following structure;

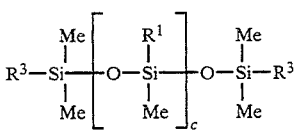

wherein;
Me is methyl;
c is an integer ranging from 1 to 200;
R¹ is selected from the group consisting of methyl and phenyl;
R³ is —(CH₂)₃—O—(CH₂—CH₂—O)$_x$—(CH₂(CH₃)CH₂—O)$_y$—(CH₂—CH₂—O)$_z$—H.

14. A process of claim 11 wherein said hydroxy silicone conforms to the following structure;

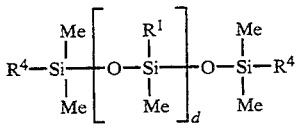

wherein;
Me is methyl;
d is an integer ranging from 10 to 1200;
R¹ is selected from the group consisting of methyl and phenyl;
R⁴ is OH.

15. A process of claim 11 wherein said poly-hydroxyl compound conforms to the following structure:

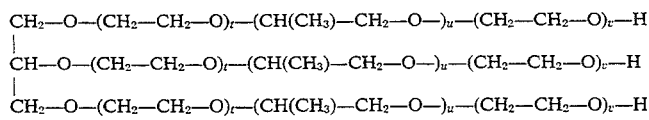

t, u and v are independently integers ranging from 0 to 20.

16. A process of claim 11 wherein said poly-hydroxyl compound conforms to the following structure:

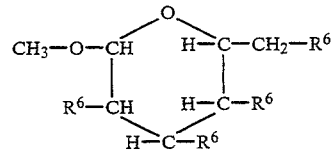

R⁶ is —O—(CH₂—CH₂—O)$_t$—(CH(CH₃)—CH₂—O—)$_u$—(CH₂—CH₂—O)$_v$—H t, u and v are independently integers ranging from 0 to 20.

17. A process of claim 11 wherein said poly-hydroxyl compound conforms to the following structure:

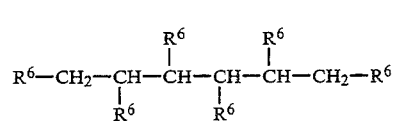

R⁶ is —O—(CH₂—CH₂—O)$_t$—(CH(CH₃)—CH₂—O—)$_u$—(CH₂—CH₂—O)$_v$—H t, u and v are independently integers ranging from 0 to 20.

18. A process of claim 11 wherein 2 wherein x+y+z is zero.

19. A process of claim 11 wherein 3 wherein x+y+z is zero.

20. A compound of claim 11 wherein the effective conditioning amount ranges from 0.05% to 25%.

* * * * *